United States Patent
Wiggins et al.

(10) Patent No.: US 9,874,615 B2
(45) Date of Patent: Jan. 23, 2018

(54) DIPOLE ARRAY ARRANGEMENT

(71) Applicant: NEW YORK UNIVERSITY, New York, NY (US)

(72) Inventors: Graham Charles Wiggins, New York, NY (US); Bei Zhang, Hartsdale, NY (US); Riccardo Lattanzi, New York, NY (US); Daniel Sodickson, Larchmont, NY (US)

(73) Assignee: New York University, New York, NY (US)

( * ) Notice: Subject to any disclaimer, the term of this patent is extended or adjusted under 35 U.S.C. 154(b) by 577 days.

(21) Appl. No.: 14/395,549

(22) PCT Filed: Apr. 19, 2013

(86) PCT No.: PCT/US2013/037468
§ 371 (c)(1),
(2) Date: Oct. 20, 2014

(87) PCT Pub. No.: WO2013/159053
PCT Pub. Date: Oct. 24, 2013

(65) Prior Publication Data
US 2015/0130465 A1   May 14, 2015

Related U.S. Application Data

(60) Provisional application No. 61/635,813, filed on Apr. 19, 2012.

(51) Int. Cl.
*G01R 33/34* (2006.01)
*G01R 33/56* (2006.01)
(Continued)

(52) U.S. Cl.
CPC .............. *G01R 33/34* (2013.01); *A61B 5/055* (2013.01); *G01R 33/56* (2013.01); *H01Q 7/00* (2013.01);
(Continued)

(58) Field of Classification Search
CPC .......... G01R 33/34; G01R 33/56; H01Q 7/00; H01Q 9/16; H01Q 9/26; H01Q 21/00; H01Q 21/20
See application file for complete search history.

(56) References Cited

U.S. PATENT DOCUMENTS 4,381,566 A   4/1983   Kane
5,462,055 A   10/1995  Casey et al.
(Continued)

FOREIGN PATENT DOCUMENTS

JP    11-056806 A    3/1999

OTHER PUBLICATIONS

Machine translation of reference GE Yokogawa Medical Systems (JP 11-056,806 A), Listed in IDS. Pub date Mar. 2, 1999.*
International Search Report for International Patent Application No. PCT/US2013/037468 dated Aug. 23, 2013.
International Written Opinion for International Patent Application No. PCT/US2013/037468 dated Aug. 23, 2013.
(Continued)

*Primary Examiner* — Rodney Bonnette
(74) *Attorney, Agent, or Firm* — Andrews Kurth Kenyon LLP

(57) ABSTRACT

An apparatus can be provided that can include a plurality of electric dipole antenna arrangements, and a processing arrangement configured to receive a signal(s) from the electric dipole antenna arrangements, and generate a magnetic resonance image based on the signal(s). Each of the electric dipole antenna arrangements can have at least two poles extending in opposite directions from each other. One of the poles can have a curved shape, which can bifurcate and follow two mirror symmetric S-shapes.

21 Claims, 9 Drawing Sheets

(51) Int. Cl.
*H01Q 7/00* (2006.01)
*H01Q 9/16* (2006.01)
*H01Q 9/26* (2006.01)
*H01Q 21/00* (2006.01)
*H01Q 21/20* (2006.01)
*A61B 5/055* (2006.01)

(52) U.S. Cl.
CPC .............. *H01Q 9/16* (2013.01); *H01Q 9/26* (2013.01); *H01Q 21/00* (2013.01); *H01Q 21/20* (2013.01)

(56) References Cited

U.S. PATENT DOCUMENTS

| | | | |
|---|---|---|---|
| 2005/0179612 A1* | 8/2005 | Holly | H01Q 23/00 343/853 |
| 2008/0228063 A1 | 9/2008 | Turner et al. | |
| 2010/0117652 A1 | 5/2010 | Cork et al. | |
| 2010/0297972 A1 | 11/2010 | Van Den Elzen | |
| 2011/0220727 A1* | 9/2011 | Lee | H01Q 1/2208 235/492 |
| 2012/0182128 A1* | 7/2012 | Ikemoto | H01Q 1/2208 340/10.1 |

OTHER PUBLICATIONS

Lattanzi R and Sodickson DK, Dyadic Green's functions . . . SNR and SAR; proceedings of the 16th Scientific Mtg of the Int'l Society for Magn Reson in Med., CA May 3-9, 2008, p. 78.

Lattanzi R. et al. Performance Evaluation of a 32-Element Head Array with Respect to the Ultimate Intrinsic SNP (2010) NMR Biomed 23(2):142-151.

Lattanzi R, Sodickson DK. Physical insights from ideal current . . . need for new designs at high field. Proceedings of the 19th Ann Mtg of ISMRM; May 7-13, 2011; Montreal. p. 3876.

Schnell W., (2000), "Ultimate signal-to-noise-ratio of surface and body antennas for magnetic resonance imagin" IEEE Trans Ant Prop 48:418-28.

Breton E. Image-Guided Radio-Frequency Gain Calibration for High-Field MRI, NMR Biomed, May 2010;28(4):368-74.

Kellman P. Image Reconstruction in SNR Units: A General Method for SNR Measurement, MRM 54:1439-1447 (2005).

Issels, Rolf D. et al., "Neo-Adjuvant Chemotherapy Alone Regional . . . ," Lancet. Oncology, vol. 11, No. 6, pp. 561-570, Jun. 2010.

Kellman, Peter et al., "Image Reconstruction in SNR Units: A General Method . . . ," Magn. Reson. Med., vol. 54, No. 6, pp. 1439-1447, Dec. 2005.

* cited by examiner

DIPOLE ARRAY ARRANGEMENT

CROSS-REFERENCE TO RELATED APPLICATION(S)

This application relates to and claims the benefit and priority from International Patent Application No. PCT/US2013/037468 filed Apr. 19, 2013, which claims the benefit of priority from U.S. Provisional Patent Application No. 61/635,813, filed on Apr. 19, 2012, the entire disclosures of which are incorporated herein by reference in their entireties.

STATEMENT REGARDING FEDERALLY SPONSORED RESEARCH

Portions of the material described herein were funded, at least in part, by National Institute of Health under grant number: RO1 EB002568. Therefore, the Federal Government may have certain rights to the invention.

FIELD OF THE DISCLOSURE

The present disclosure generally relates to a medical imaging apparatus, and more specifically, to exemplary embodiments of an electric dipole antenna array.

BACKGROUND INFORMATION

Analysis of the Ultimate Intrinsic Signal-To-Noise Ratio ("UISNR") through a current mode expansion employing dyadic Green's functions ("DGF") (See, e.g., 1 and 2) can make it possible to plot the current pattern on a given surface which can result in the UISNR for a given position in the phantom, which can be called the ideal current pattern (See, e.g., References 1 and 3). For a cylindrical phantom with a concentric cylindrical surface, the ideal current pattern which maximizes central signal to-noise ratio ("SNR") can look like a pair of distributed loops at low field (See, e.g., FIG. 1, section 110). At high fields, however, the ideal current pattern for central SNR can assume a pattern that can be a mixture of loops and electric dipole components (See, e.g., Reference 3).

A contribution of the latter to UISNR can increase with frequency (See, e.g., References 3 and 4) and, for certain geometries, the ideal current pattern can be dominated by electric dipole currents, in which the current can flow in straight lines along the length of the cylinder with no return path (See, e.g., FIG. 1, section 120). Traditionally, a common antenna structure for magnetic resonance imaging ("MRI") can be a surface coil loop. Although conventional stripline coils or transverse electro-magnetic ("TEM") elements can appear to mimic an electric dipole antenna, both can rely on the presence of a closely coupled shield, which can provide a return path, and therefore can support loops of current rather than electric dipole currents.

Thus, there may be a need to address and/or overcome at least some of the above-described deficiencies.

SUMMARY OF EXEMPLARY EMBODIMENTS

To address at least some of these drawbacks and/or deficiencies, exemplary embodiments of the present disclosure can be provided which can implement an array of electric dipole antennas, for example, to mimic the ideal current pattern. The exemplary electric dipole antennas can be used to transmit or receive RF signals. For example, electric dipole antenna arrays can be used for hyperthermia therapy to steer heating into deep tissues. (See e.g., Reference 5). Due to the nature of exemplary ideal current patterns there can be exemplary embodiments where electric dipole antennas can provide superior performance than conventional magnetic loop antennas. According to further exemplary embodiments of the present disclosure, it is possible to provide a combination of electric dipole antennas and magnetic loop antennas can provide superior performance than either type of antenna on its own. Exemplary embodiments of the present disclosure, therefore, can include, for example, an array of 8 electric dipole antennas on a cylinder, and, for example, an array combining 8 electric dipole antennas and 8 magnetic loop antennas.

According to certain exemplary embodiments of the present disclosure, arrangements, methods, and computer readable mediums can be provided which can include, utilize and/or implement an RF coil array arrangement, for example, which can include: a plurality of electric dipole antennas; and a processing arrangement configured to: receive signals from the electric dipole antennas and determine a Magnetic Resonance Image. In certain exemplary embodiments, at least one pole of at least one electric dipole antenna can be provided that can have two mirror symmetric S-shapes. According to certain exemplary embodiments, a plurality of electric dipole antennas can be combined with a plurality of magnetic loop antenna elements.

According to certain exemplary embodiments, a plurality of electric dipole antennas and magnetic loop antennas can be combined with a parallel transmit arrangement which transmits RF power through a plurality of electric dipole antennas or to a combination of electric dipole antennas and magnetic loop antenna elements. In certain exemplary embodiments of the present disclosure, a heat controller can be provided that can be connected to the electric dipole antennas, and which can be configured to deposit heat to a target area of a biological structure.

In some exemplary embodiments of the present disclosure, a receiving element(s) can be configured to receive the signal(s), which can be based on a further signal(s) transmitted by the electric dipole antenna arrangements, and send the signal(s) to the processing arrangement. The electric dipole antenna arrangements can be configured to transmit a further signal(s), receive the signal(s) which is based on the further signal(s), and send the signal(s) to the processing arrangement. In certain exemplary embodiments of the present disclosure, one of the magnetic loop antenna arrangement(s) or the electric dipole antenna arrangements can be configured to transmit a further signal(s), and the other one of the magnetic loop antenna arrangement(s) or the electric dipole antenna arrangements can be configured to receive the signal(s) which can be based on the further signal(s), and transmit the signal(s) to the processing arrangement.

In a further exemplary embodiment of the present disclosure, arrangements, methods, and computer readable mediums can be provided which can include, utilize and/or implement the electric dipole antenna array arrangement that can comprise, for example, a plurality of electric dipole antenna elements, each including two poles extending in substantially opposite directions. For example, at least part of each pole can bifurcate and then follow curves such that a length of each pole can be longer than a distance between a start of each pole and a distal end of each pole. In certain exemplary embodiments of the present disclosure the part of each pole that can be bifurcated can form two mirror symmetric S-shape curves. In certain exemplary embodiments of the present disclosure, the part of each of the poles that curves can be located at or near the distal end of each such pole. According to additional exemplary embodiments of the present disclosure, a processing arrangement can be provided which can be connected to the plurality of electric dipole antenna elements, and which can be configured to receive signals from the electric dipole antenna elements and determine data associated with a Magnetic Resonance Image.

These and other objects of the present disclosure can be achieved by provision of an apparatus that can include a plurality of electric dipole antenna arrangements, and a processing arrangement configured to receive a signal(s) from the electric dipole antenna arrangements and generating a magnetic resonance image based on signal(s). Each of the electric dipole antenna arrangements can have at least two poles extending in opposite directions from each other. The poles can have a curved shape, which can bifurcate and follow two mirror symmetric S-shapes. The mirror symmetric S-shapes can be located at or near a distal end of the pole(s). The electric dipole antenna arrangements can include at least 8 electric dipole antenna arrangements, which can be arranged in the shape of a cylinder.

In certain exemplary embodiments of the present disclosure, a radiation arrangement can be coupled to the electric dipole antenna arrangements, which can be configured to provide a radiation to a target area of a biological structure. The electric dipole antennas can be configured to receive the radiation from the radiation arrangement, and direct a resultant radiation to the target area. The radiation can include a radio frequency signal(s).

In some exemplary embodiments of the present disclosure, a magnetic loop antenna arrangement(s) can be configured to operate in conjunction and simultaneously with the electric dipole antenna arrangements. The magnetic loop antenna arrangement(s) can at least 8 magnetic loop antenna elements.

In a further embodiment of the present disclosure is an electric dipole antenna array arrangement, which can include a plurality of electric dipole antenna arrangements, each of the electric dipole antenna arrangements can include at least two poles extending in substantially opposite directions. A particular(s) end of the poles can be curved, and a length of each of the poles can be longer than a distance between a proximal end of a particular one of the poles and a distal end of the particular one of the poles. The particular end(s) can have a form of an S-shape, which can be bifurcated, and then follow a mirror symmetric S-shaped path.

In certain exemplary embodiments of the present disclosure, a processing arrangement can be coupled to the electric dipole antenna arrangements, and can be configured to receive a signal(s) from the electric dipole antenna arrangements, and generate a magnetic resonance image based on the signal(s). In some exemplary embodiments of the present disclosure, a plurality of magnetic dipole arrangements can be configured to operate in conjunction and simultaneously with the electric dipole antenna arrangements. The electric dipole antenna arrangements can include at least 8 electric dipole antenna arrangements, and the magnetic dipole arrangements can include at least 8 magnetic dipole arrangements.

These and other objects, features and advantages of the present disclosure will become apparent upon reading the following detailed description of exemplary embodiments of the present disclosure, when taken in conjunction with the accompanying exemplary drawings and appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 1 is an illustration of an ideal current pattern at low and high field; to;

Figure 1:
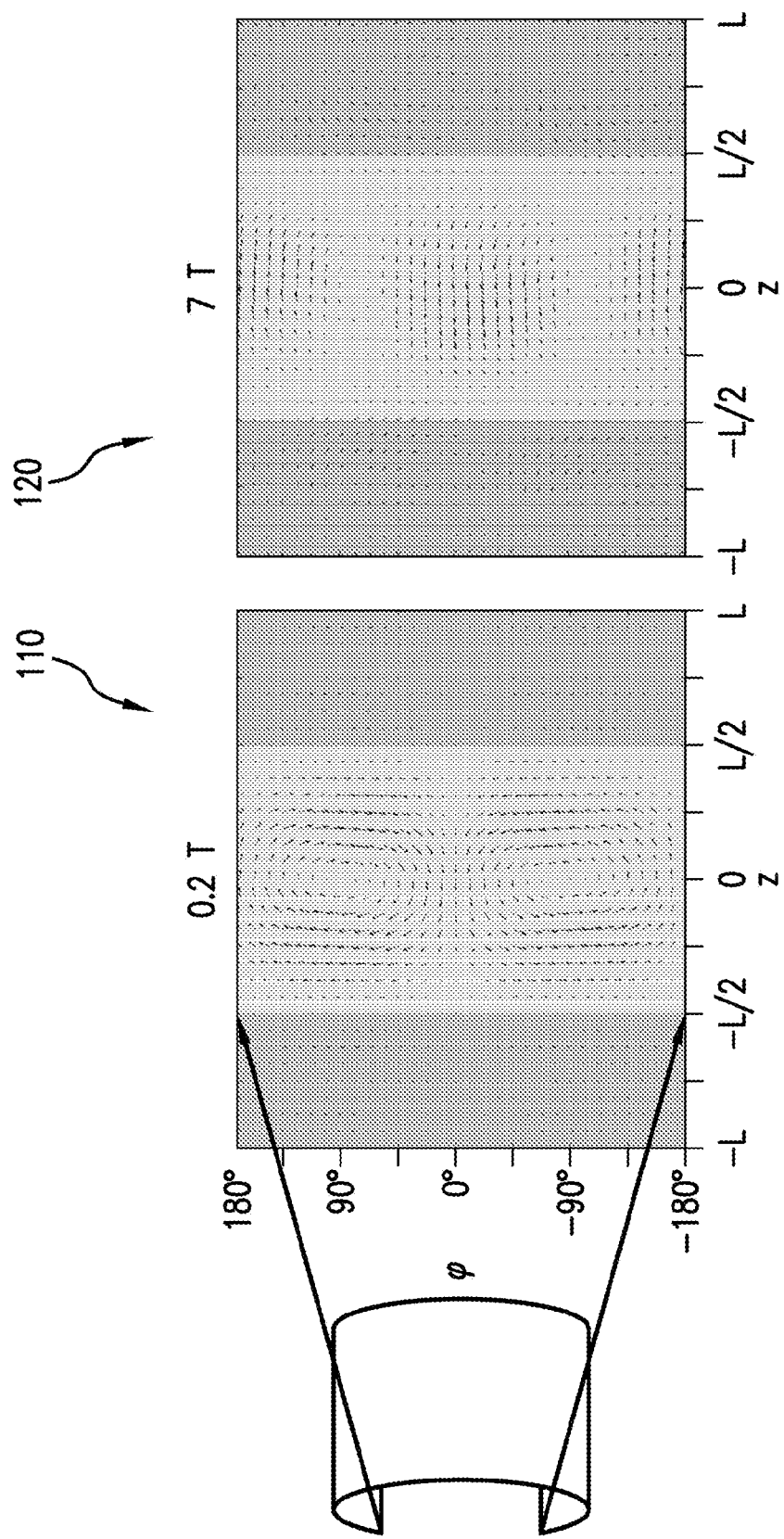

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures or the accompanying claims.

DETAILED DESCRIPTION OF EXEMPLARY EMBODIMENTS

Figure 2:
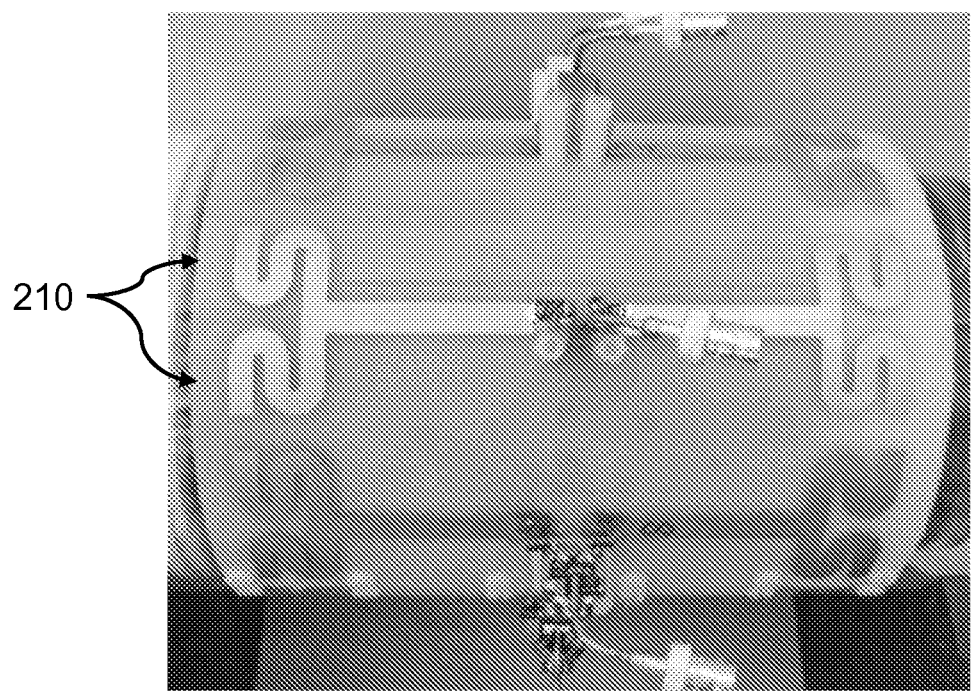
FIG. 2 is an illustration of an exemplary folded electric dipole antenna array according to an exemplary embodiment of the present disclosure.
Figure 3:
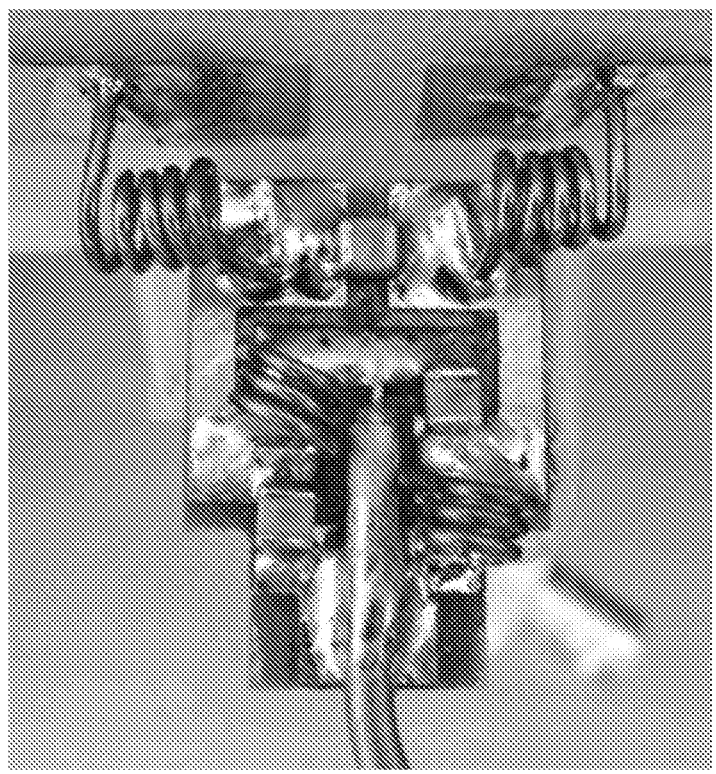
FIG. 3 is an illustration of an exemplary match circuit according to an exemplary embodiment of the present disclosure.

According to exemplary embodiments of the present disclosure, an electric dipole antenna and/or methods for making/using the same can be provided. In the exemplary electric dipole antennas, exemplary maximum efficiency can be achieved when the length of the antenna can be equal to about ½ the free space wavelength of the electromagnetic wave that can be transmitted or received. For example, in the case of 7 Tesla, this can correspond to a length of approximately 50 cm, which can be impractical for certain applications. In certain exemplary embodiments, the electric dipole antenna can be shortened with some loss of efficiency by adopting an exemplary folded dipole design, such as shown in FIG. 2.

According to certain exemplary embodiments of the present disclosure, the exemplary electric dipole antenna array can include certain exemplary arrangements of the conductors, for example, to shorten the length of the electric dipole antenna. One exemplary way to accomplish this shortening can be with the exemplary S-shapes 210, as shown in FIG. 2. According to certain exemplary embodiments of the present disclosure, electromagnetic simulations can be exhibited, which can indicate that the current pattern on a cylinder, for example, which can correspond to the ultimate possible sensitivity, can have greater electric dipole-like properties than magnetic loop-like properties. For example, at low field, the ultimate sensitivity can come from loops of current, although at high field, the ultimate sensitivity can come from current patterns which can resemble an electric dipole. Thus, the exemplary electric dipole antennas which can be used to excite and receive signals for MR imaging can provide a surprising benefit over previously known antennas that avoid the use of electric dipole antennas for MRI applications. According to exemplary embodiments of the present disclosure, the ultimate sensitivity can come from current patterns which can contain a mixture of electric dipole and magnetic loop components. Thus, the exemplary combinations of electric dipole antennas and magnetic loop elements, which can be used to excite and receive signals for MR imaging, can provide receive sensitivity or parallel transmit performance substantially greater than can be obtained with either type of element used alone.

Figure 5:
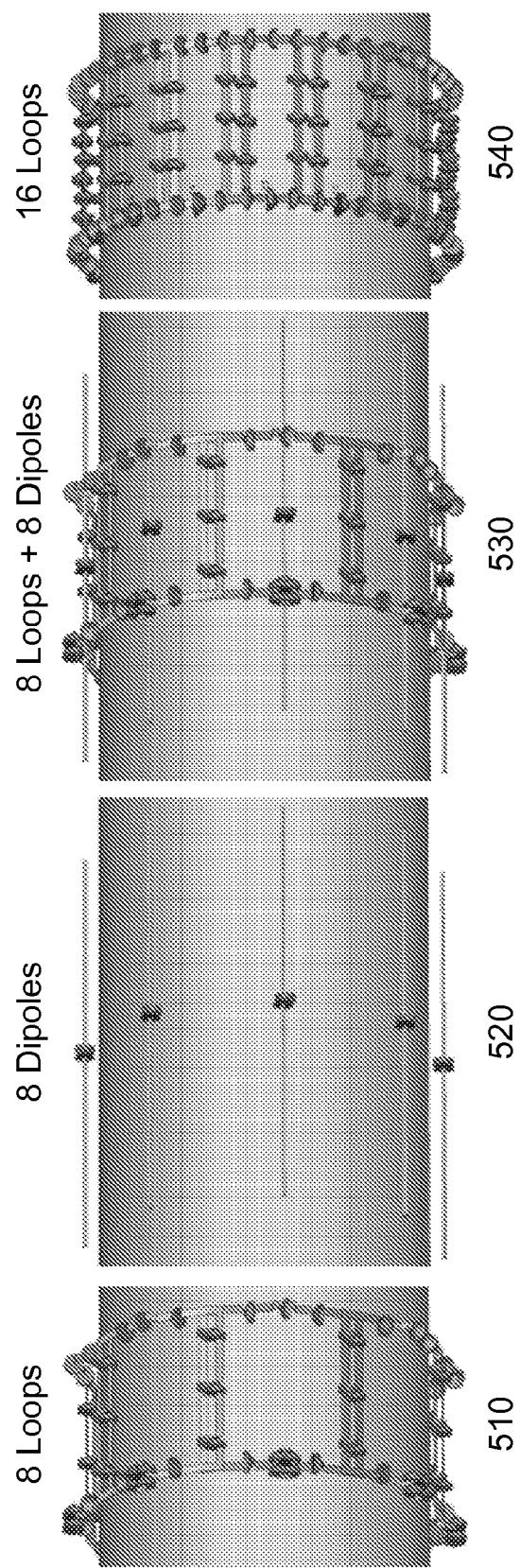
FIG. 5 is an illustration of an exemplary illustration of exemplary dipole coil according to an exemplary embodiment of the present disclosure.

As shown in FIG. 5, various exemplary coils can be simulated and constructed on, e.g., identical 31.5 cm diameter cylindrical surfaces (e.g. an 8-element magnetic loop antenna array 510, an 8-element electric dipole antenna array 520 and an array that can include 8 electric dipole antennas and 8 magnetic loop antenna elements 530). For example, an exemplary array 540, which can include 16 magnetic loop antenna elements, can also be simulated. The exemplary coils can surround a 29.5 cm diameter cylindrical phantom (e.g., element 640 of FIG. 6) with $\epsilon_r$=81.8 and $\sigma$=0.604 s/meter. Simulations can be conducted using an exemplary finite difference time domain method (e.g., Microwave Studio, CST, Framingham Mass.). An array of, e.g., 8 overlapped magnetic loop antenna elements 510 about 14.6 cm×15 cm in size can be simulated and constructed. A single row of 8 electric dipole antennas 520 can be simulated and also constructed, with each element self-resonant with a conductor length of 35.6 cm (See e.g., FIG. 1b). A 16 element array 530 can be simulated and constructed which can include a single row of 8 overlapped magnetic loop antennas with approximately 35.6 cm long electric dipole antenna centered over each magnetic loop antenna. Additionally, a single row of, e.g., 16 overlapped 7.3×15 cm magnetic loop antenna elements 540 can be simulated. All coil elements can be tuned and matched in the simulation, and driven with 50 Ohm ports. As shown in FIG. 7, a constructed magnetic loop antenna 710 can be fashioned from tinned bus wire incorporating 11 distributed capacitors and matched to coax with λ/4 lattice baluns 720.

The exemplary electric dipole antennas 730 can be made from, e.g., FR4 circuit board with 7 mm wide traces having lengths adjusted between 32 cm and 36 cm to fine-tune them according to their proximity to the phantom. All or most elements can be matched to coaxes with λ/4 lattice baluns. The exemplary coil can be connected to the scanner using in-house constructed T/R coil interface boxes. For the exemplary electric dipole and the exemplary combined electric dipole and magnetic loop experiments, the electric dipole antennas can be used to transmit. For the exemplary electric dipole or the exemplary magnetic loop experiments the unused coil elements can be defeated by removal of capacitors, or by cutting through the electric dipole antenna conductors. In each experiment equal power can be supplied to each channel, and phase can be adjusted to provide circularly polarized excitation at the center of the phantom.

The exemplary data can be acquired on, e.g., a 7 Tesla whole body scanner (e.g., Siemens Medical Solutions, Erlangen, Germany) with an 8 channel parallel transmit system. SNR maps for the optimal combination (See e.g., Reference 6), and can be generated from GRE acquisitions with and without RF excitation (e.g., TR/TE/Flip/BW=1000/3.39/20/300, FoV=400 mm, Matrix=128, Slice=5mm) after calibrating the excitation flip angle at the center of the phantom. B1+ maps with matched FoV and matrix can be generated using the AFI technique (See e.g., Reference 7), acquiring maps with transmit phases corresponding to the "uniform" birdcage mode. and then with the first gradient mode, as well as corresponding low flip angle GRE magnitude images. Exemplary normalized SNR maps can be obtained by dividing the SNR maps by the sine of the measured flip angle at each pixel.

Exemplary Results

Exemplary derivation of the UISNR for the center of the phantom can illustrate that curl-free (e.g., electric dipole-like) currents can provide 21% higher SNR than magnetic loop-like currents, and that facilitating both types of currents can provide 54% higher SNR than magnetic loop-like currents alone. Exemplary CST simulations achieved S11 match of better than −18 dB on all ports and maximum S12 coupling of −13.7 dB. Simulation of the exemplary map of 8 electric dipole antennas 820 alone can provide a 3.1% boost compared to the exemplary map of 8 magnetic loop antennas 810. However, the exemplary map of the combination of the two antennas 830 can provide an SNR boost of 24% (See e.g., FIG. 8). This additional SNR may not only be attributed to the increased number of elements in the combined array, since the simulation with, e.g., the exemplary map of 16 magnetic loop antennas 840 may only provide approximately 1.2% SNR increase compared to 8 magnetic loop antennas.

Figure 9:
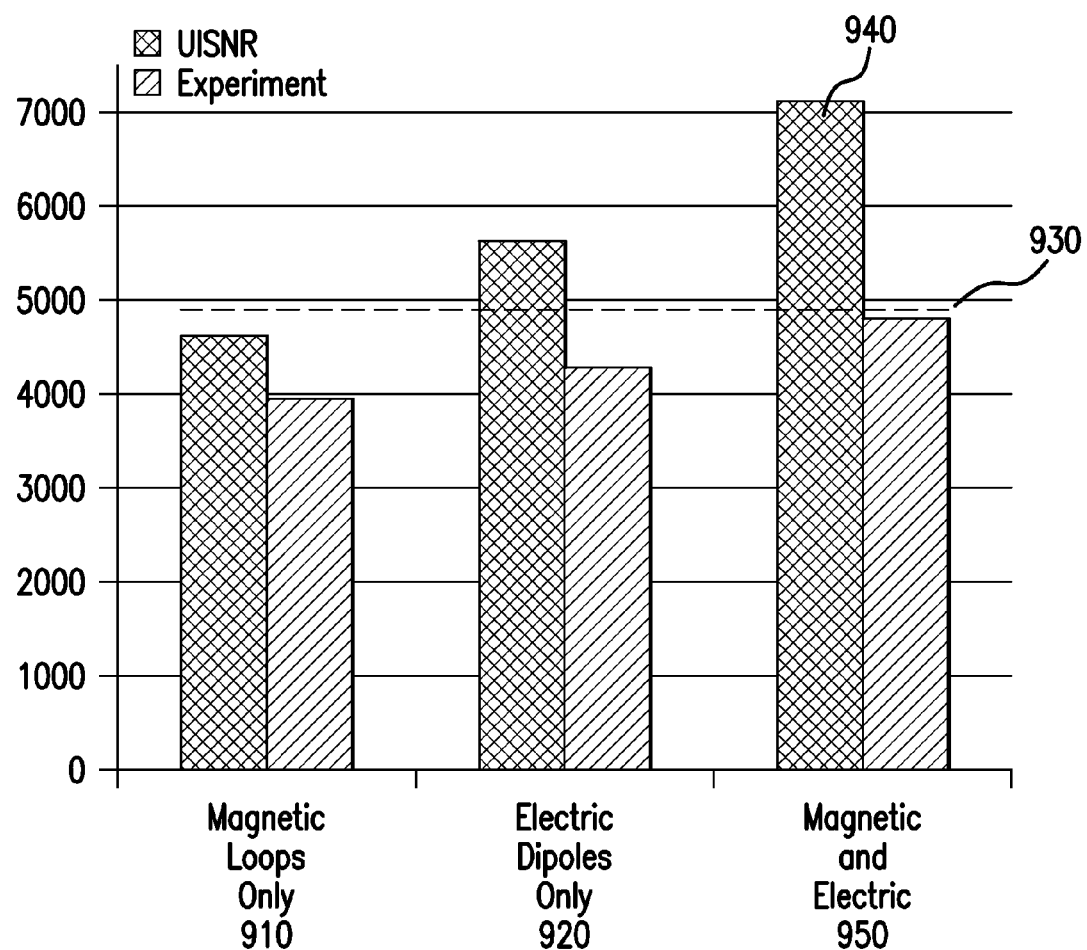
FIG. 9 is an exemplary chart illustrating the Ultimate Intrinsic Signal-To-Noise Ratio and experimental Signal-To-Noise Ratio according to an exemplary embodiment of the present disclosure.

For the exemplary coil, the overall pattern of SNR can be very close to the simulated results. Experimental results with the exemplary map of 8 electric dipole antennas alone 860 can provide an 8.3% boost as compared to the exemplary map of 8 magnetic loop antennas 850, which can be higher than the 3.1% found in simulation. Using the exemplary maps of combined magnetic loop antennas and electric dipole antennas 860 can provide a 22% boost, very close to the 24% boost found in simulation. Using the exemplary dimensions of the coil surface and phantom, as well as the phantom electrical properties, the ultimate intrinsic SNR for the center of the phantom can be calculated, scaled to account for the acquisition parameters used in the exemplary experiments. (See e.g., Reference 8). For exemplary 8 magnetic loop antennas can capture 85.6% of the magnetic loop-only UISNR (e.g., element 910 of FIGS. 9), and 8 electric dipole antennas can capture about 76.0% of the electric dipole-only UISNR (e.g., element 920 of FIG. 9). The coil combining magnetic loop antennas and electric dipole antennas can achieve a central SNR higher than the UISNR for magnetic loop currents only (elements 930 and 940 of FIG. 9). This can demonstrate that combining electric dipole antennas and magnetic loop antennas can provide receive sensitivity that can be higher than that which can be obtained with any previously known or conceivable array of magnetic loop antennas. Greater diversity of the high field ideal current patterns can be captured, which can provide a significant performance gain.

Certain electromagnetic simulations have shown that in some circumstances, particularly at high field or for large objects, for example, the highest possible sensitivity for an MR antenna can be obtained if the antenna can support current patterns that can be electric dipole-like, and not composed of loops of current. Thus, use of exemplary electric dipole antennas can provide a superior sensitivity, as compared to magnetic loop antennas or shielded stripline elements, particularly at high field and for large objects. Further, the exemplary use of the exemplary electric dipole antennas, combined with conventional magnetic loop antennas, can provide a better sensitivity compared to what can be possible even with an array of a large number of magnetic loop antenna elements at high field and for large objects. According to certain exemplary embodiments of the present disclosure, it can be possible to utilize mirror image meanders, for example, to shorten the electric dipole antenna which can make it possible to create a shorter antenna that can still be resonant at the desired frequency, for example, without the incorporation of lossy lumped elements.

Exemplary electric dipole antennas for both heating of the body and magnetic resonance ("MR") imaging can facilitate certain functions to be performed by, for example, a single coil structure. Phase and magnitude of the RF signal to different elements can be controlled to steer the heating to the desired region, while applying high RF power, for example to heat tumors. The exemplary location of the tumor can be determined by, for example, using the same antenna for MR imaging. Additionally, the exemplary MR image can be used to measure the temperature in the tumor through the use of MR thermometry, using the same structure for all purposes. This can also be applied at lower fields where the MR sensitivity of the electric dipole antennas can be lower than a conventional coil, yet still sufficient for imaging, while providing simultaneous application as a heat delivery device.

According to further exemplary embodiments of the present disclosure, certain exemplary electric dipole antennas can differ from existing "stripline" coil designs in that they may not incorporate a close proximity ground plane, which can limit the efficiency of shielded stripline elements, and can cause them to differ in behavior from the current patterns which can maximize efficiency.

Exemplary Combined Electric Dipole Antenna and Magnetic Loop Antenna Array

Figure 6:
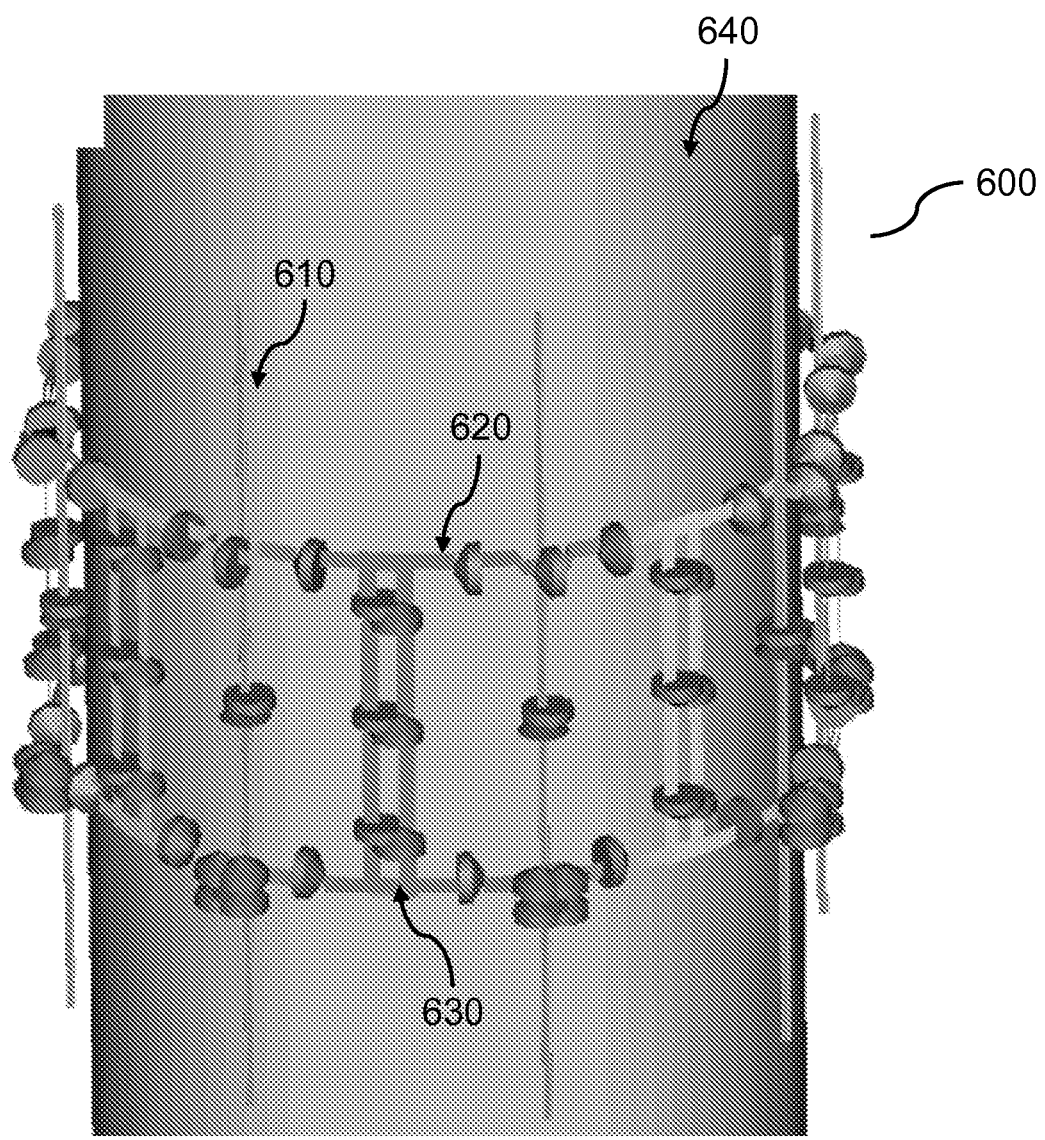
FIG. 6 is an illustration of an exemplary combined electric dipole antenna and magnetic loop antenna array according to an exemplary embodiment of the present disclosure.
Figure 7:
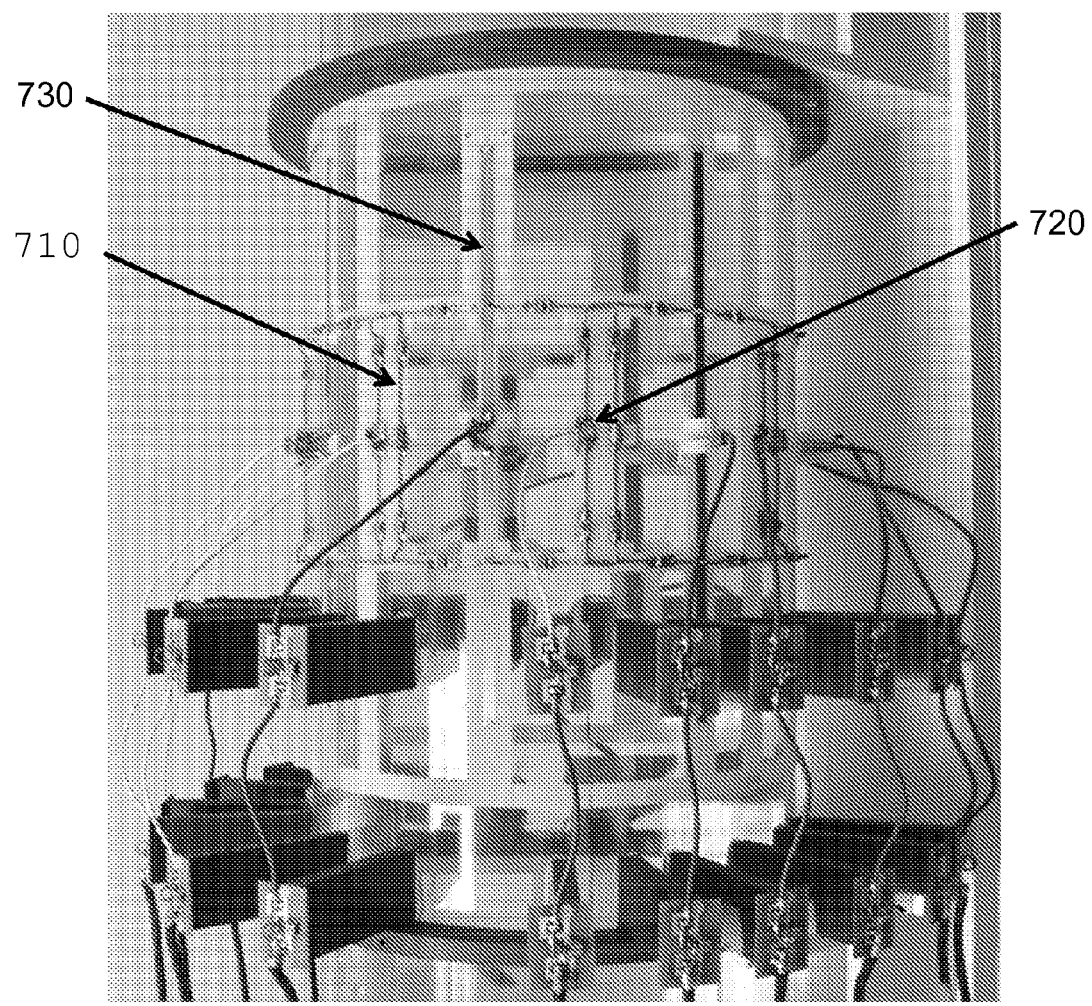
FIG. 7 is an exemplary image of an exemplary combined electric dipole antenna and magnetic loop antenna array implementation according to an exemplary embodiment of the present disclosure.

FIG. 6 illustrates an exemplary 7 Tesla Combined Electric Dipole Antenna and Magnetic Loop Antenna Array 600. Each electric dipole antenna 610 can have a magnetic loop antenna 620 placed symmetrically on top of it, for example, to minimize inductive coupling between the magnetic loop antenna and electric dipole antenna. Neighboring magnetic loop antennas can be overlapped (e.g., as shown at 630) to minimize inductive coupling. The configuration can include any number of settings, dimensions, parameters, and/or attributes, and FIG. 6 can illustrate a phantom 640 with a diameter=29.5 cm ($\epsilon r$=60, s=0.61 S/m), an array diameter=31.5 cm, an electric dipole antenna length=36 cm, and a magnetic loop antenna size=14.6 cm×15 cm. FIG. 7 shows an exemplary image illustrating an exemplary combined electric dipole antenna and magnetic loop antenna array implementation according to certain exemplary embodiments of the present disclosure.

Figure 8:
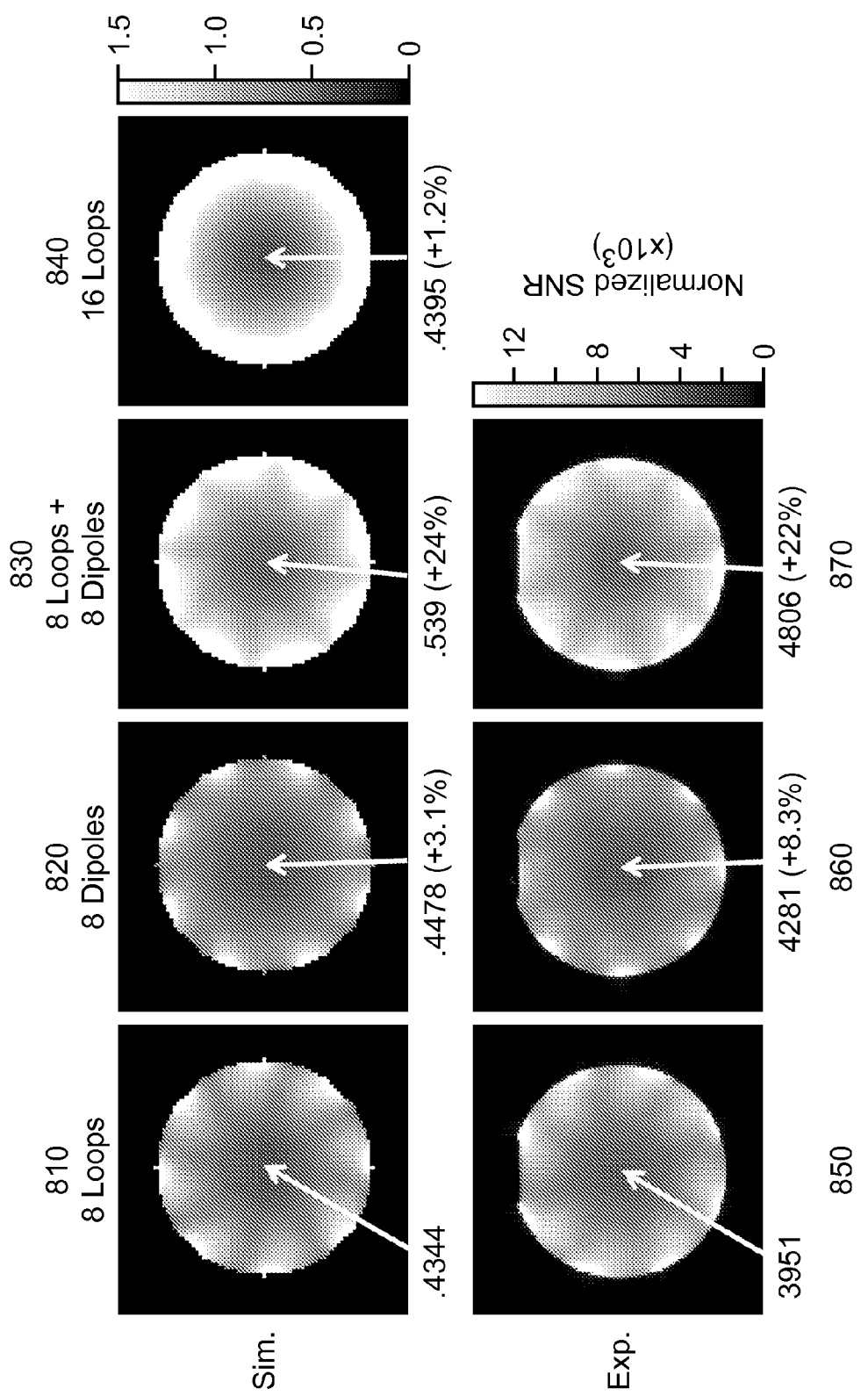
FIG. 8 is a set of illustrations of exemplary signal-to-noise ratio maps according to an exemplary embodiment of the present disclosure.

FIG. 8 illustrates exemplary SNR maps obtained by electromagnetic simulation and the exemplary experimentation of certain exemplary embodiments. For example, map 810 illustrates a simulated SNR map for 8 magnetic loop antennas alone (e.g., with a central SNR of 0.4344), the exemplary map 820 illustrates a simulated SNR map for 8 electric dipole antennas alone (e.g., with a central SNR of 0.44780.2838), the exemplary map 830 illustrates a simulated SNR map for 8 electric dipole antennas and 8 magnetic loop antennas combined (e.g., with a central SNR of 0.539), and the exemplary map 840 illustrates a simulated SNR map for 16 magnetic loop antennas alone (e.g., with a central SNR of 0.4395). Additionally, the exemplary map 850 illustrates an experimental SNR map for 8 magnetic loop antennas alone (e.g., with a central SNR of 3951), the exemplary map 860 illustrates an experimental SNR map 860 for 8 electric dipole antennas alone (e.g., with a central SNR of 4281), and the exemplary map 870 illustrates an experimental SNR map for 8 electric dipole antennas and 8 magnetic loop antennas (e.g., with a central SNR of 4806). As the exemplary simulated and experimental SNR maps can indicate, the SNR of 8 electric dipole antennas combined with 8 magnetic loop antennas can be higher than 8 electric dipole antennas alone and/or 8 magnetic loop antennas alone.

Exemplary Dipole Antenna System

Figure 4:
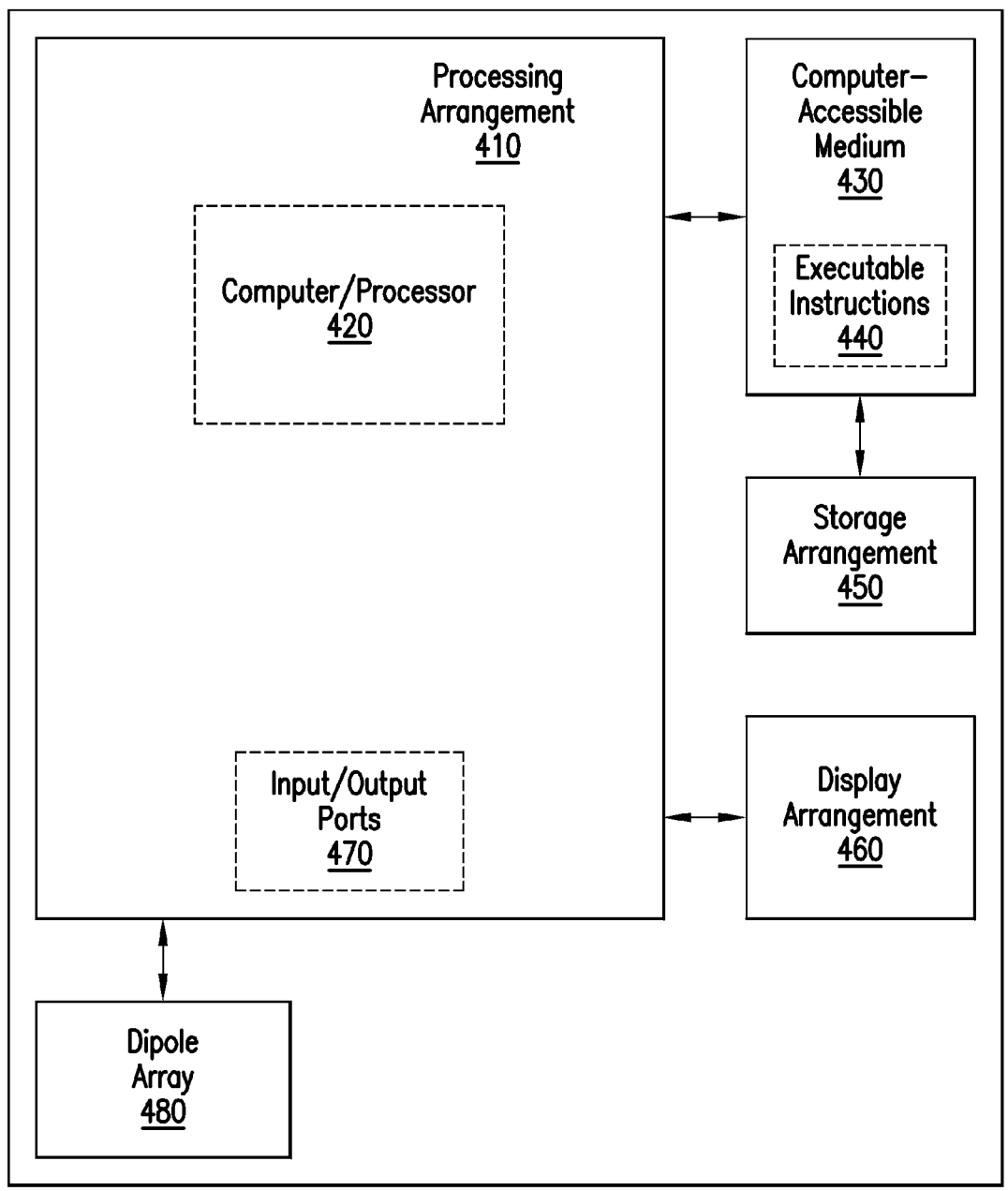
FIG. 4 is an exemplary system, including an exemplary computer-accessible medium, according to an exemplary embodiment of the present disclosure.

FIG. 4 shows a block diagram of an exemplary embodiment of a system according to the present disclosure. For example, exemplary procedures in accordance with the present disclosure described herein can be performed by a processing arrangement and/or a computing arrangement 410 and an electric dipole antenna array arrangement 480. Such processing/computing arrangement 410 can be, for example, entirely or a part of, or include, but not limited to, a computer/processor 420 that can include, for example, one or more microprocessors, and use instructions stored on a computer-accessible medium (e.g., RAM, ROM, hard drive, or other storage device).

As shown in FIG. 4, for example, a computer-accessible medium 430 (e.g., as described herein above, a storage device such as a hard disk, floppy disk, memory stick, CD-ROM, RAM, ROM, etc., or a collection thereof) can be provided (e.g., in communication with the processing arrangement 410). The computer-accessible medium 430 can contain executable instructions 440 thereon. In addition or alternatively, a storage arrangement 450 can be provided separately from the computer-accessible medium 430, which can provide the instructions to the processing arrangement 410 so as to configure the processing arrangement to execute certain exemplary procedures, processes and methods, as described herein above, for example.

Further, the exemplary processing arrangement 410 can be provided with or include an input/output arrangement 470, which can include, for example, a wired network, a wireless network, the interne, an intranet, a data collection probe, a sensor, etc. As shown in FIG. 4, the exemplary processing arrangement 410 can be in communication with an exemplary display arrangement 460, which, according to certain exemplary embodiments of the present disclosure, can be a touch-screen configured for inputting information to the processing arrangement in addition to outputting information from the processing arrangement, for example. Further, the exemplary display 460 and/or a storage arrangement 450 can be used to display and/or store data in a user-accessible format and/or user-readable format.

The foregoing merely illustrates the principles of the disclosure. Various modifications and alterations to the described embodiments will be apparent to those skilled in the art in view of the teachings herein, and especially in the appended numbered paragraphs. It will thus be appreciated that those skilled in the art will be able to devise numerous systems, arrangements, and methods which, although not explicitly shown or described herein, embody the principles of the disclosure and are thus within the spirit and scope of the disclosure. In addition, all publications and references referred to above are incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement which can be a microprocessor, mini, macro, mainframe, etc. In addition, to the extent that the prior art knowledge has not been explicitly incorporated by reference herein above, it is explicitly being incorporated herein in its entirety. All publications referenced above are incorporated herein by reference in their entireties.

EXEMPLARY REFERENCES

The following references are hereby incorporated by reference in their entirety.
[1] Lattanzi R. (2008) ISMRM p. 78
[2] Lattanzi R. (2010) NMR Biomed 23 (2):142-51
[3] Lattanzi R. (2011), ISMRM p.
[4] Schnell W. (2000), IEEE Trans Ant Prop 48:418-28.
[5] Issels R. Lancet Oncology 2010; 11:561-70
[6] Kellman P. MRM 54:1439-1447 (2005)
[7] Yarnykh; Magn Reson Med, 2007. 57 (1):192-200
[8] Lattanzi R. NMR Biomed 23 (2):142-51 (2010)

What is claimed is:

1. An apparatus comprising:
a plurality of electric dipole antenna arrangements, wherein each of the electric dipole antenna arrangements has at least two poles extending in opposite directions from each other; and
a processing arrangement configured to receive at least one signal from the electric dipole antenna arrangements, and generating a magnetic resonance image based on the at least one signal.

2. The apparatus of claim 1, wherein at least one of the poles has a curved shape.

3. The apparatus of claim 2, wherein the curved shape bifurcates and follows two mirror symmetric S-shapes.

4. The apparatus of claim 3, wherein the mirror symmetric S-shapes are located at or near a distal end of the at least one pole.

5. The apparatus of claim 1, wherein the electric dipole antenna arrangements comprise at least 8 electric dipole antenna arrangements.

6. The apparatus of claim 5, wherein the electric dipole antenna arrangements are arranged in the shape of a cylinder.

7. The apparatus of claim 1, further comprising a radiation arrangement coupled to the electric dipole antenna arrangements, the radiation arrangement being configured to provide a radiation to a target area of a biological structure.

8. The apparatus of claim 7, wherein the electric dipole antennas are configured to receive the radiation from the radiation arrangement, and direct a resultant radiation to the target area.

9. The apparatus of claim 7, wherein the radiation comprises at least one radio frequency signal.

10. The apparatus of claim 1, further comprising at least one magnetic loop antenna arrangement configured to operate in conjunction and simultaneously with the electric dipole antenna arrangements.

11. The apparatus of claim 10, wherein at least one of the at least one magnetic loop antenna arrangement or the electric dipole antenna arrangements is configured to transmit at least one further signal, and wherein at least one of the at least one magnetic loop antenna arrangement or the electric dipole antenna arrangements is configured to receive the at least one signal which is based on the at least one further signal, and transmit the at least one signal to the processing arrangement.

12. The apparatus of claim 1, further comprising at least one receiving element configured to receive the at least one signal based on at least one further signal transmitted by the electric dipole antenna arrangements, and transmit the at least one signal to the processing arrangement.

13. An apparatus comprising:
a plurality of electric dipole antenna arrangements;
a processing arrangement configured to receive at least one signal from the electric dipole antenna arrangements, and generating a magnetic resonance image based on the at least one signal; and
at least one magnetic loop antenna arrangement configured to operate in conjunction and simultaneously with the electric dipole antenna arrangements, wherein the at least one magnetic loop antenna arrangement comprises at least 8 magnetic loop antenna arrangements.

14. An apparatus comprising:
a plurality of electric dipole antenna arrangements; and
a processing arrangement configured to receive at least one signal from the electric dipole antenna arrangements, and generating a magnetic resonance image based on the at least one signal, wherein the electric dipole antenna arrangements are configured to transmit at least one further signal, receive the at least one signal which is based on the at least one further signal, and transmit the at least one signal to the processing arrangement.

15. An electric dipole antenna array arrangement, comprising:
a plurality of electric dipole antenna arrangements, each of the electric dipole antenna arrangements including at least two poles extending in substantially opposite directions;
wherein at least one particular end of the poles is curved; and
wherein a length of each of the poles is longer than a distance between a proximal end of a particular one of the poles and a distal end of the particular one of the poles.

16. The arrangement of claim 15, wherein the at least one particular end has a form of an S-shape.

17. The arrangement of claim 16, wherein the at least one particular end is bifurcated, and then follows a mirror symmetric S-shaped path.

18. The arrangement of claim 15, further comprising a processing arrangement coupled to the electric dipole antenna arrangements, wherein the processing arrangement is configured to receive at least one signal from the electric dipole antenna arrangements, and generate a magnetic resonance image based on the at least one signal.

19. The arrangement of claim 15, further comprising a plurality of magnetic dipole arrangements configured to operate in conjunction and simultaneously with the electric dipole antenna arrangements.

20. The arrangement of claim 19, wherein the electric dipole antenna arrangements comprises at least 8 electric dipole antenna arrangements, and the magnetic dipole arrangements comprises at least 8 magnetic dipole arrangements.

21. An antenna arrangement, comprising:
a plurality of electric dipole antenna array arrangements, wherein each of the electric dipole antenna arrangements has at least two poles extending in opposite directions from each other; and
a plurality of magnetic dipole array arrangements cooperating with the electric dipole antenna array arrangements.

\* \* \* \* \*

UNITED STATES PATENT AND TRADEMARK OFFICE
CERTIFICATE OF CORRECTION

PATENT NO. : 9,874,615 B2
APPLICATION NO. : 14/395549
DATED : January 23, 2018
INVENTOR(S) : Graham Charles Wiggins et al.

It is certified that error appears in the above-identified patent and that said Letters Patent is hereby corrected as shown below:

In the Specification

Please amend the third paragraph under Column 1, Lines 14-20 with the following paragraph as follows:

Statement Regarding Federally Sponsored Research
This invention was made with government support under grant number R01 EB002568 awarded by the National Institutes of Health. The government has certain rights in this invention.

Signed and Sealed this
Eleventh Day of June, 2019

Andrei Iancu
*Director of the United States Patent and Trademark Office*